(12) United States Patent
Steffens et al.

(10) Patent No.: US 8,409,124 B2
(45) Date of Patent: Apr. 2, 2013

(54) BLOOD PUMP SYSTEM USER INTERFACE ALARM MANAGEMENT

(75) Inventors: Brian J. Steffens, Maple Grove, MN (US); Mark Salzwedel, Eden Prairie, MN (US); Mark G. Bearss, Minnetonka, MN (US); Bruce R. Jones, Champlin, MN (US); Beth C. Bullemer, Maple Plain, MN (US); William K. Wenger, St. Paul, MN (US)

(73) Assignee: Medronic, Inc., Minneapolis, MN (US)

( * ) Notice: Subject to any disclaimer, the term of this patent is extended or adjusted under 35 U.S.C. 154(b) by 661 days.

(21) Appl. No.: 11/977,916

(22) Filed: Oct. 26, 2007

(65) Prior Publication Data
US 2008/0221495 A1   Sep. 11, 2008

Related U.S. Application Data

(60) Provisional application No. 60/905,640, filed on Mar. 8, 2007.

(51) Int. Cl.
*A61M 37/00* (2006.01)

(52) U.S. Cl. .................................. 604/4.01

(58) Field of Classification Search ............ 604/4.01; 417/43
See application file for complete search history.

(56) References Cited

U.S. PATENT DOCUMENTS

| | | | | |
|---|---|---|---|---|
| 4,524,354 A | * | 6/1985 | Morgan | 340/825.36 |
| 5,881,723 A | * | 3/1999 | Wallace et al. | 128/204.21 |
| 5,956,023 A | * | 9/1999 | Lyle et al. | 715/771 |
| 5,999,918 A | * | 12/1999 | Williams et al. | 705/36 R |
| 6,031,354 A | * | 2/2000 | Wiley et al. | 320/116 |
| 6,071,258 A | * | 6/2000 | Dalke et al. | 604/5.01 |
| 6,359,444 B1 | * | 3/2002 | Grimes | 324/633 |
| 6,783,328 B2 | | 8/2004 | Lucke et al. | |
| 6,918,887 B1 | | 7/2005 | Gremel et al. | |
| 7,022,099 B2 | | 4/2006 | Litzie et al. | |
| 7,022,284 B2 | | 4/2006 | Brian et al. | |
| 7,108,672 B2 | * | 9/2006 | Steele et al. | 604/6.01 |
| 7,117,438 B2 | * | 10/2006 | Wallace et al. | 715/709 |
| 7,201,870 B2 | | 4/2007 | Olsen et al. | |
| 7,278,981 B2 | * | 10/2007 | Ellingboe et al. | 604/4.01 |
| 7,354,415 B2 | * | 4/2008 | Bainbridge et al. | 604/6.01 |
| 7,776,001 B2 | * | 8/2010 | Brugger et al. | 604/5.01 |
| 2002/0085952 A1 | * | 7/2002 | Ellingboe et al. | 422/45 |
| 2003/0135152 A1 | * | 7/2003 | Kollar et al. | 604/35 |
| 2004/0111471 A1 | * | 6/2004 | Stoner et al. | 709/204 |
| 2004/0149282 A1 | * | 8/2004 | Hickle | 128/203.14 |
| 2004/0243048 A1 | * | 12/2004 | Brugger et al. | 604/4.01 |
| 2006/0140798 A1 | * | 6/2006 | Kutsuzawa | 417/474 |
| 2006/0167400 A1 | * | 7/2006 | Ellingboe et al. | 604/6.14 |
| 2006/0238358 A1 | * | 10/2006 | Al-Ali et al. | 340/573.1 |
| 2007/0048181 A1 | * | 3/2007 | Chang et al. | 422/57 |
| 2007/0219532 A1 | * | 9/2007 | Karpowicz et al. | 604/540 |
| 2008/0046469 A1 | * | 2/2008 | Ikeguchi et al. | 707/104.1 |
| 2008/0221418 A1 | * | 9/2008 | Al-Ali et al. | 600/324 |
| 2009/0247851 A1 | * | 10/2009 | Batchelder et al. | 600/324 |
| 2009/0248319 A1 | * | 10/2009 | Call et al. | 702/22 |
| 2009/0315684 A1 | * | 12/2009 | Sacco et al. | 340/10.6 |

* cited by examiner

*Primary Examiner* — Susan Su

(57) ABSTRACT

User interfaces for medical perfusion systems that provide oxygenation, filtering, and recirculation of blood in connection with various medical procedures are provided. In particular, user interfaces for use with blood pumps that assist in managing alarms commonly encountered during cardiopulmonary bypass surgeries are provided.

19 Claims, 10 Drawing Sheets
(7 of 10 Drawing Sheet(s) Filed in Color)

BLOOD PUMP SYSTEM USER INTERFACE ALARM MANAGEMENT

CROSS-REFERENCE TO RELATED APPLICATION

The present application claims priority to U.S. Provisional Application No. 60/905,640, filed Mar. 8, 2007, the entire contents of which are incorporated herein by reference.

TECHNICAL FIELD

The present invention is directed to user interfaces for medical perfusion systems that provide oxygenation, filtering, and recirculation of blood in connection with various medical procedures. In particular, the present invention is directed to user interfaces for use with blood pumps that assist in managing alarms commonly encountered during cardiopulmonary bypass surgeries.

BACKGROUND

Conventional perfusion systems are used to oxygenate, filter, and/or recirculate the blood of a patient during a medical procedure such as during cardiopulmonary surgeries. Such perfusion systems include a fluid conduit that removes blood from the patient during the medical procedure, a separate fluid conduit that returns blood to the patient, one or more blood pumps that pump blood through the conduits, and a plurality of sensing devices, such as flow sensors and/or level sensors associated with blood pumps. The perfusion system may also include air embolus sensors, temperature sensors, flow occluders, etc.

Perfusion systems require a perfusionist operating the perfusion system to closely monitor many different parameters, and manually adjust the speeds of the various pumps in the system on a frequent basis to keep the various parameters in balance and within safe and desired limits. Alarm conditions, when they occur, require immediate, manual action by the perfusionist. Accordingly, mechanisms are needed to help the perfusionist safely, accurately, and quickly manage such alarm conditions control the perfusion system with greater safety, accuracy and speed.

SUMMARY

The present invention provides unique user interface designs that annunciates an alarm condition, describes the nature of the alarm with indicia such as text, and provides the user with options concerning how to best manage the alarm condition. Clear visual indicators are provided to assist in managing the device and handling the alarm condition. For example, visual indicators may use the colors red and yellow to guide the user to quickly manage the machine interface during the management of alarms.

In an aspect of the present invention, a method of managing an alarm condition of a perfusion system during cardiopulmonary bypass surgery is provided. The method comprises the steps of providing a user interface for the perfusion system comprising a touch screen, displaying a color coded alarm condition on the touch screen, and displaying a color coded alarm management icon on the touch screen for managing the displayed color coded alarm condition.

In another aspect of the present invention, a user interface for managing an alarm condition of a perfusion system during cardiopulmonary bypass surgery is provided. The user interface comprises a touch screen, a color coded alarm condition indicator displayed on the touch screen comprising a color coded graphical portion and a color coded textual message portion for providing information related to an alarm condition, one or more color-coded alarm management icons displayed on the display screen for managing the alarm condition based on the color coded alarm condition indicator.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of this application, illustrate several aspects of the invention and together with description of the embodiments serve to explain the principles of the invention. A brief description of the drawings is as follows.

DETAILED DESCRIPTION

Figure 1:
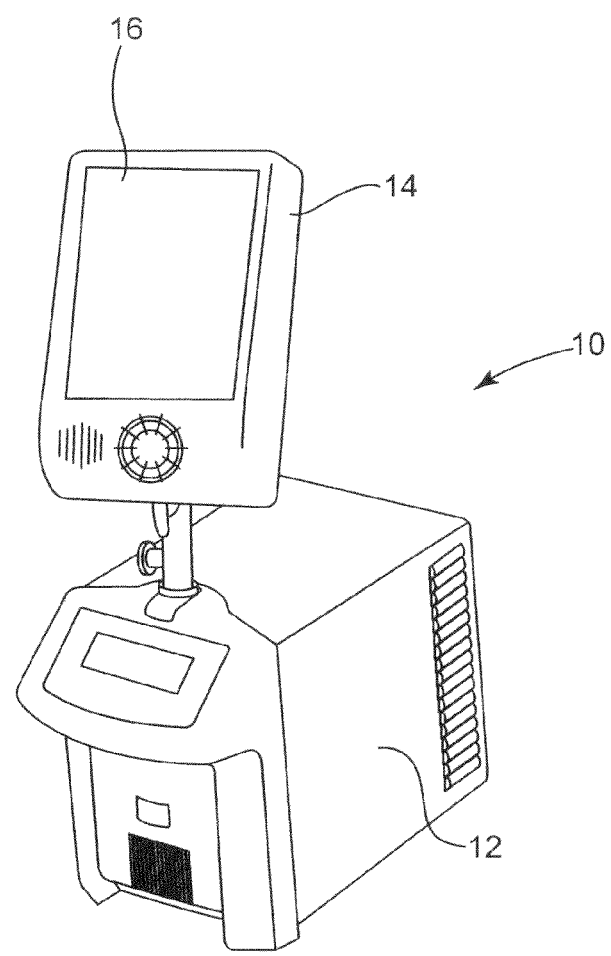
FIG. 1 is a perspective view of an exemplary pump console according to an aspect of the present invention showing a user interface and a base unit.
Figure 2:
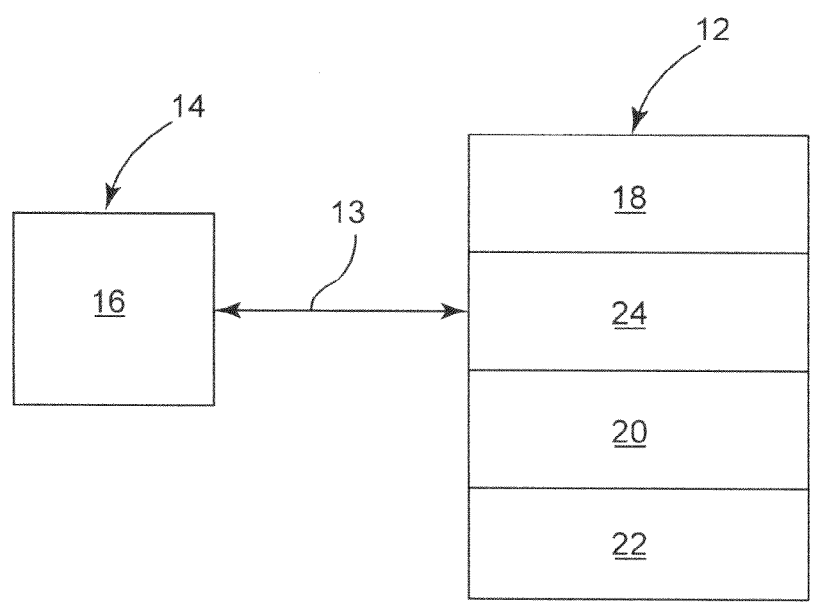
FIG. 2 is a schematic block diagram of the pump console of FIG. 1.

FIG. 1 is an exemplary perspective view and FIG. 2 is a schematic block diagram of a pump console 10 in accordance with the present invention. As shown, the pump console 10 comprises two primary components, including a base unit 12 and a user interface 14 that can communicate via communication link 13. The pump console 10 may comprise a stand-alone centrifugal pump control system or it may comprise an add-on module to commercially available heart-lung machines or blood pumps. The base unit 12 provides functionality for controlling pump speed, monitoring flow/pressure, battery backup, and providing communications to the user interface 14, for example. The user interface 14 includes a display 16 and user controls for operating and/or interfacing with the user interface 14. Display 16 preferably comprises a touch display/screen or other display device that allows input to be provided to an icon displayed on the screen by touching, contacting, or otherwise identifying the icon. Components of the base unit 12 and/or user interface 14 preferably comprise microcontrollers that provide communications through an asynchronous serial interface (RS232) or suitable communications protocol.

Figure 3:
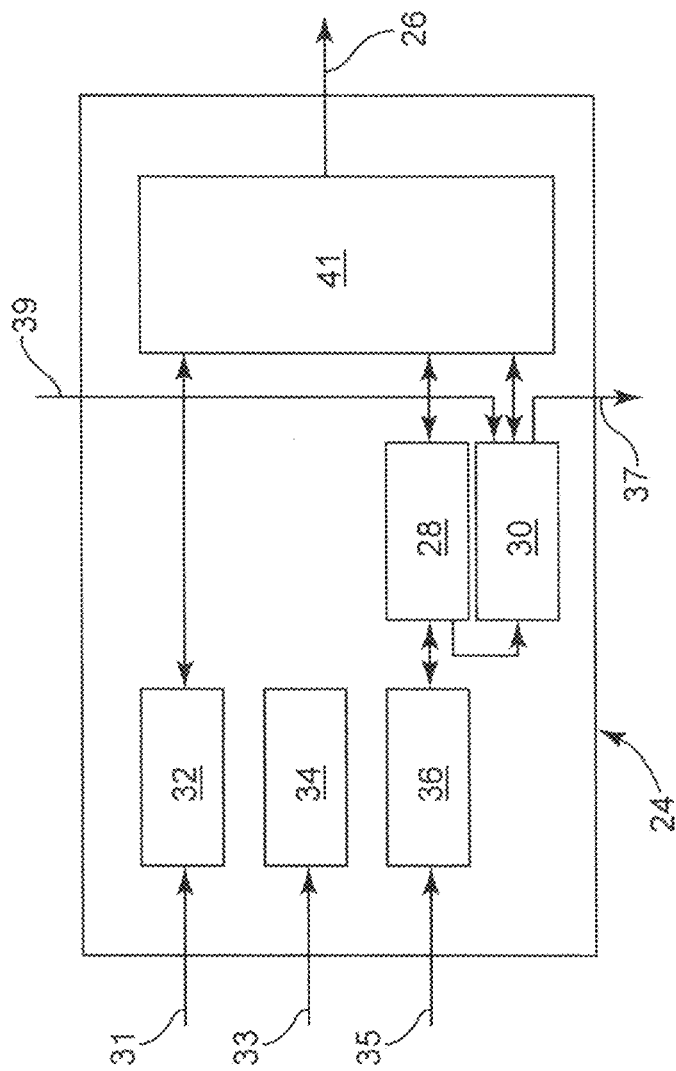
FIG. 3 is a schematic diagram of a safety module that can be used with the base unit according to an aspect of the present invention.

As illustrated, the base unit 12 comprises plural functional modules including a system controller module 18, motion/pressure module 20, flow module 22, and safety module 24. The safety module 24 is schematically shown in further detail in FIG. 3 and preferably comprises a safety module bus interface 41, system bus interface 26, watchdog timer 28, and motor controller servo interface 30, which motor controller includes speed control input 39 and speed control output 37. The safety module 24 also preferably includes interfaces to safety systems such as a bubble detector interface 32, level sensor interface(s) 34, and an arterial clamp interface 36, which comprise inputs 31, 33, and 35, respectively. The bubble detector interface 32 provides an alarm to the operator when it detects the presence of bubbles or gross air in the tubing of the flow circuit. The level sensor interface(s) 34 provide an alarm or alert to the operator preferably based upon two separate level detectors placed on the patient blood reservoir. The arterial clamp interface 36 provides automated arterial line occlusion in the event of retrograde flow as determined by operator setup.

Figure 4:
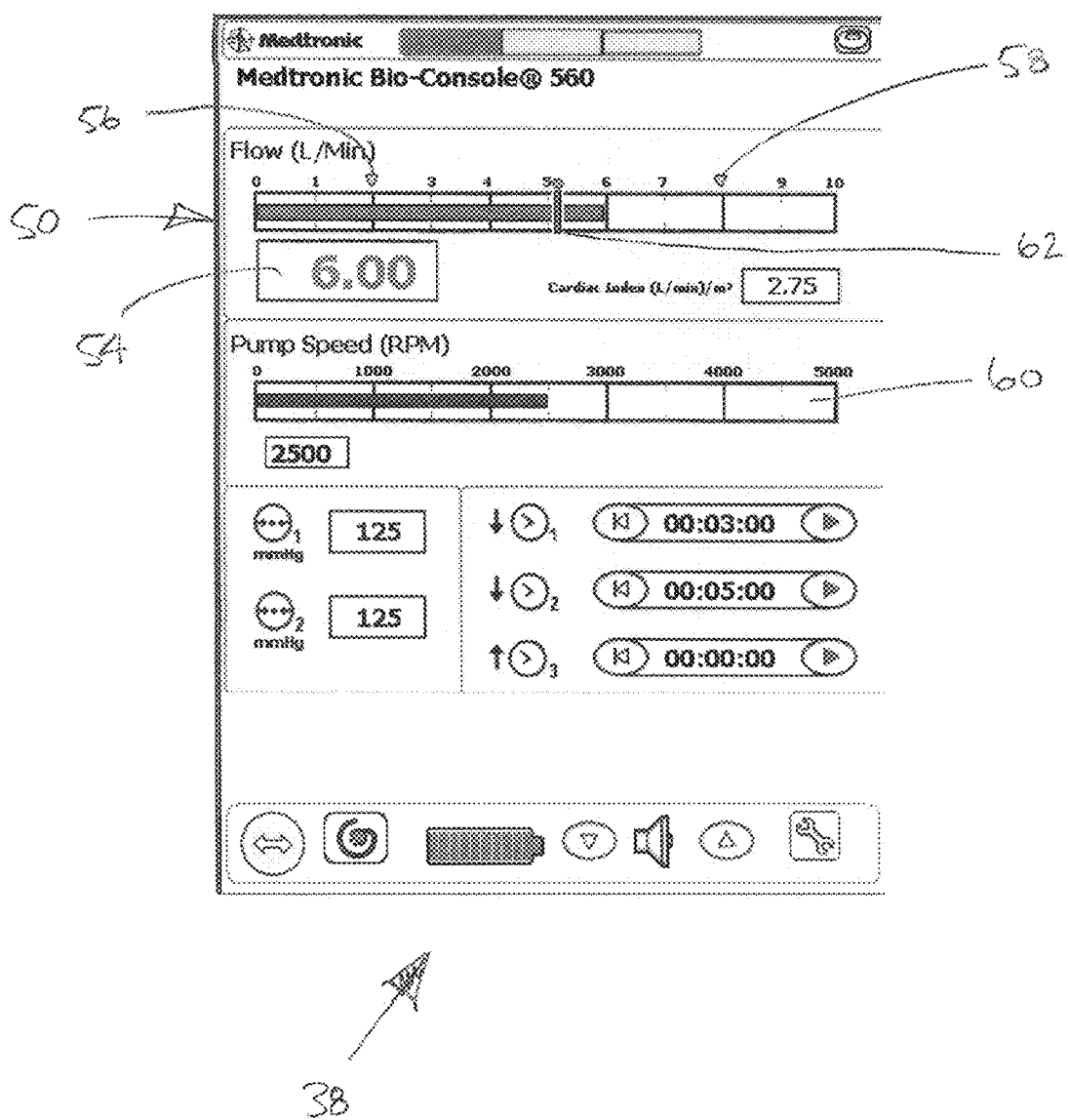
FIG. 4 is an exemplary main screen of a user interface in accordance with the present invention.

FIG. 4 illustrates an exemplary main screen 38 for the user interface 14 in accordance with the present invention. In use, main screen 38, as well as any other screen or screens of the user interface 14, are displayed on display 16 and are preferably capable of receiving touch inputs such as with a finger or appropriate stylus. Main screen 38 is preferably configured to display information related to operating parameters such as alert and alarm status, blood flow and pump speed, line pressure, user configurable timers, safety systems (if installed), and power status, for example.

Figure 5:
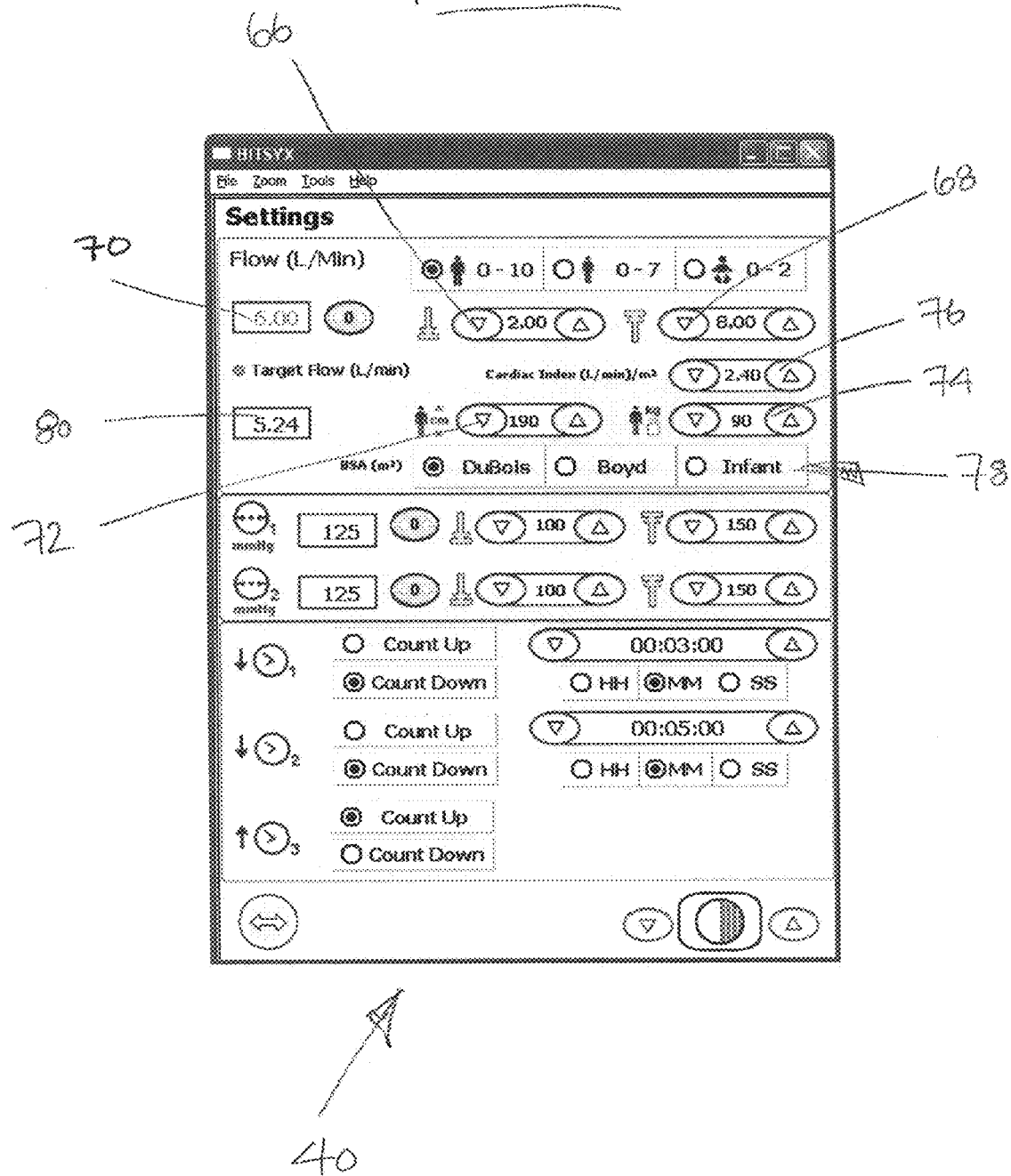
FIG. 5 is an exemplary settings screen of a user interface in accordance with the present invention.

An exemplary settings screen 40 of the user interface 14 is shown in FIG. 5. Settings screen 40 provides the capability to set parameters such as blood flow range and upper/lower alert/alarm limits, target blood flow rate with cardiac index and height/weight calculator, pressure transducer zeroing and upper/lower alert/alarm limits, three timer presets, and screen backlight intensity, for example.

User interface 14 preferably comprises a system status indicator 42 positioned at the top of a desired user interface screen such as those shown in FIGS. 3, 8, 22, 26, and 27. System status indicator 42 preferably comprises an optional color-coded status bar 44 and a color-coded system status message box 46. The color coded status bar 44 preferably uses three colored light bars 48, 50, and 52 that are associated with the operation status of the system and provide a visual cue for assessing system status when lit. Preferably first, second, and third colors such as green, yellow, and red are used for the light bars 48, 50, and 52, respectively, however any desired colors can be used. The status bar 44 and message box 46, as shown, are preferably positioned at the top of a screen but can be positioned anywhere on a screen as desired. The intensity of the light bars 48, 50, and 52 as well as any other color coded icon of the user interface can be varied to provide additional visual information such as the intensity of a condition, alert, or alarm.

The user interface 14 preferably uses distinct alarm/alert sounds or audible signals to inform the user when alarm or alert conditions are present. An alarm sound preferably comprises a repeating sequence of long and short beeps. An alarm condition is more serious than an alert condition and requires a corrective action by the user. An alert sound preferably comprises a steady paced beep.

Figure 6:
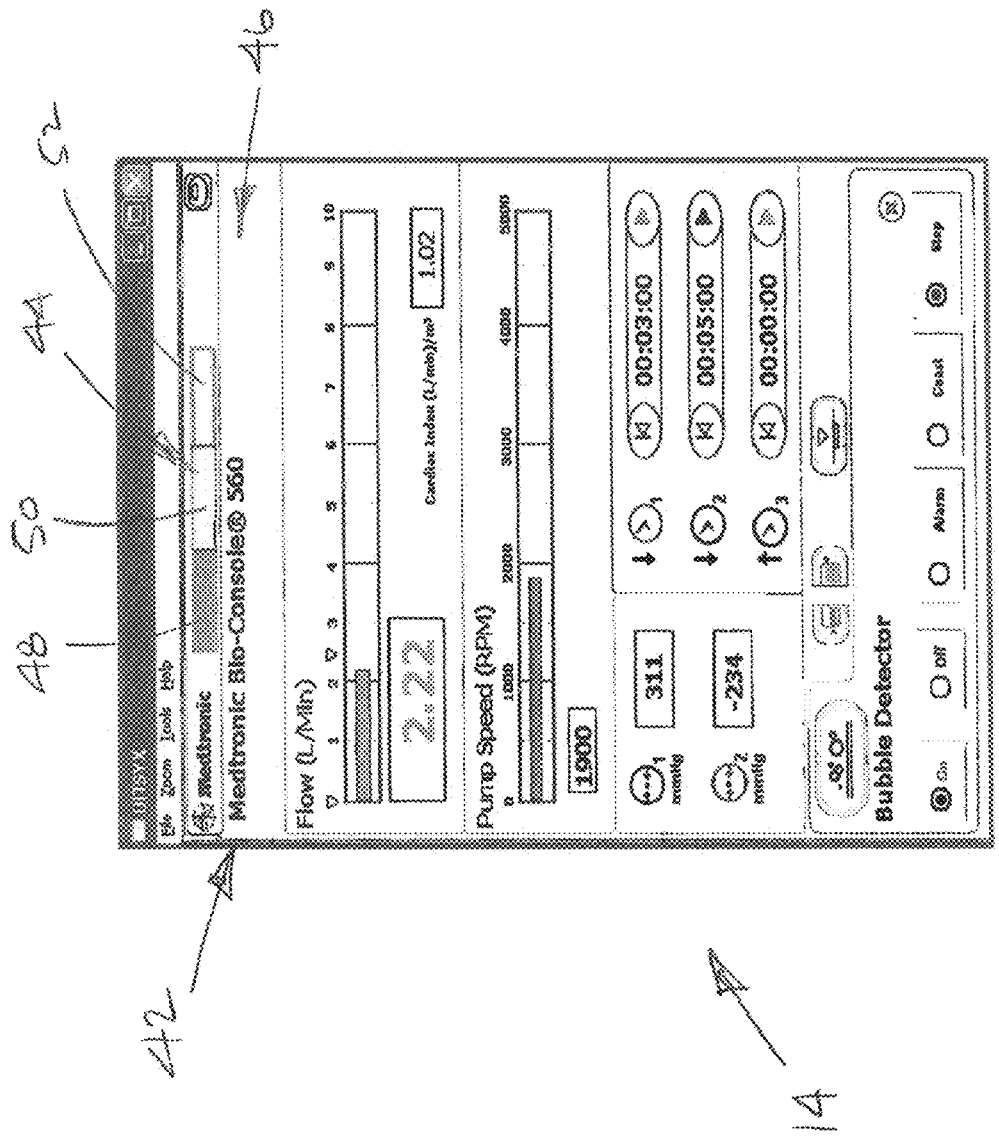
FIG. 6 illustrates a user interface in accordance with the present invention in a normal state of operation without an indication of an alert or alarm condition.

In FIG. 6, user interface 14 is illustrated in a state of normal operation. That is, no alert or alarm conditions are active. As shown, illumination of the green light bar 48 of the system status indicator 42 indicates all systems are functioning normally and (as applicable) safety devices are enabled. In this normal state, light bars 50 and 52 are unlit or colorless. Accordingly, no action is indicated or required to keep the system functioning normally in such system state. Additionally, the system status message box 46 displays information about the highest priority alert or alarm. The user interface 14 is preferably pre-programmed so that alerts or alarms are prioritized. Preferably, the highest priority alert or alarm is displayed and when that alert or alarm is corrected the next highest alert or alarm is displayed, if any. In the normal state of operation and as illustrated in FIG. 6, the system status message box 46 is preferably displayed without a corresponding green color code although the system status message box 46 may be color coded if desired. That is, message box 46 can be white or grey, for example, or match the background color of other screen elements as desired.

Figure 7:
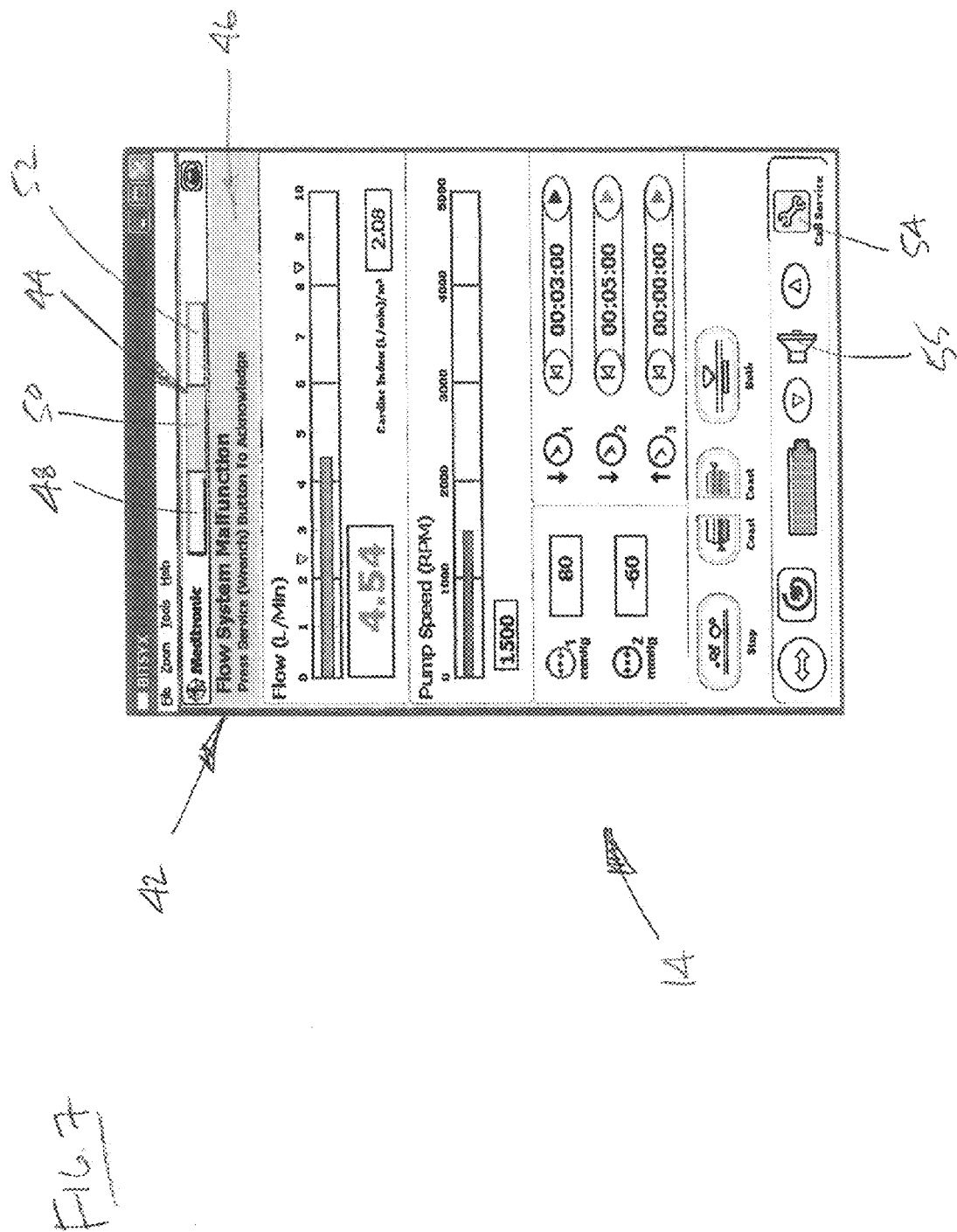
FIG. 7 illustrates a user interface in accordance with the present invention showing an alert condition identified by a color coded status bar and a color coded message box and showing color coded information for managing the alert condition.

In FIG. 7, user interface 14 is illustrated in a state of malfunction and with an indication of an alert. An alert indicates a condition other than normal operation and that requires attention by an operator. In this case, the state of malfunction is a flow-system malfunction. An alert notification preferably includes a steady paced beep or other audible signal and illumination of the yellow light bar 50 of the system status indicator 42, as illustrated. Light bars 48 and 52 are preferably unlit or colorless, as illustrated. Additionally, the system status message box 46 displays information about the alert and is preferably displayed with a corresponding yellow color code. The system is preferably configured so an alert or alarm condition is preferably temporarily silenced by pressing the mute button 55, but will preferably resume after 60 seconds if the condition is not resolved or if a new alert or alarm condition occurs. The mute button 55 preferably only appears when an alert or alarm condition exists and may be color-coded if desired.

The illustrated alert condition of FIG. 7 is a flow system malfunction but any desired condition can be characterized as an alert condition. Exemplary alert conditions include those related to a low reservoir, flow rate, pressure, and clamp air pressure. An alert condition indicates a problem and typically requires a corrective action by the user. The system status message box 46 identifies the alert condition and also provides information regarding how to manage the alert condition using the words "Press Service (Wrench) Button To Acknowledge." The alert condition can be managed by pressing the service wrench button 54, which is also preferably color-coded, yellow with the alert condition color. Pressing the service wrench button 54 displays a log of internal system errors. An alert condition may display additional unique yellow icons to aid the user in identifying the source of the alert condition. The user interface 14 thus provides an indication of the alert condition with the yellow light bar 50 and yellow coded system status message box 46, indication of the particular alert condition and how to manage the alert condition in the system status message box 46, and an indication of where to manage the alert condition on the touch screen with the color coded icon (e.g., service wrench button 54). Any combination of colors, color intensity, sounds, and text can be used in accordance with the present invention to identify an alert condition.

Figure 8:
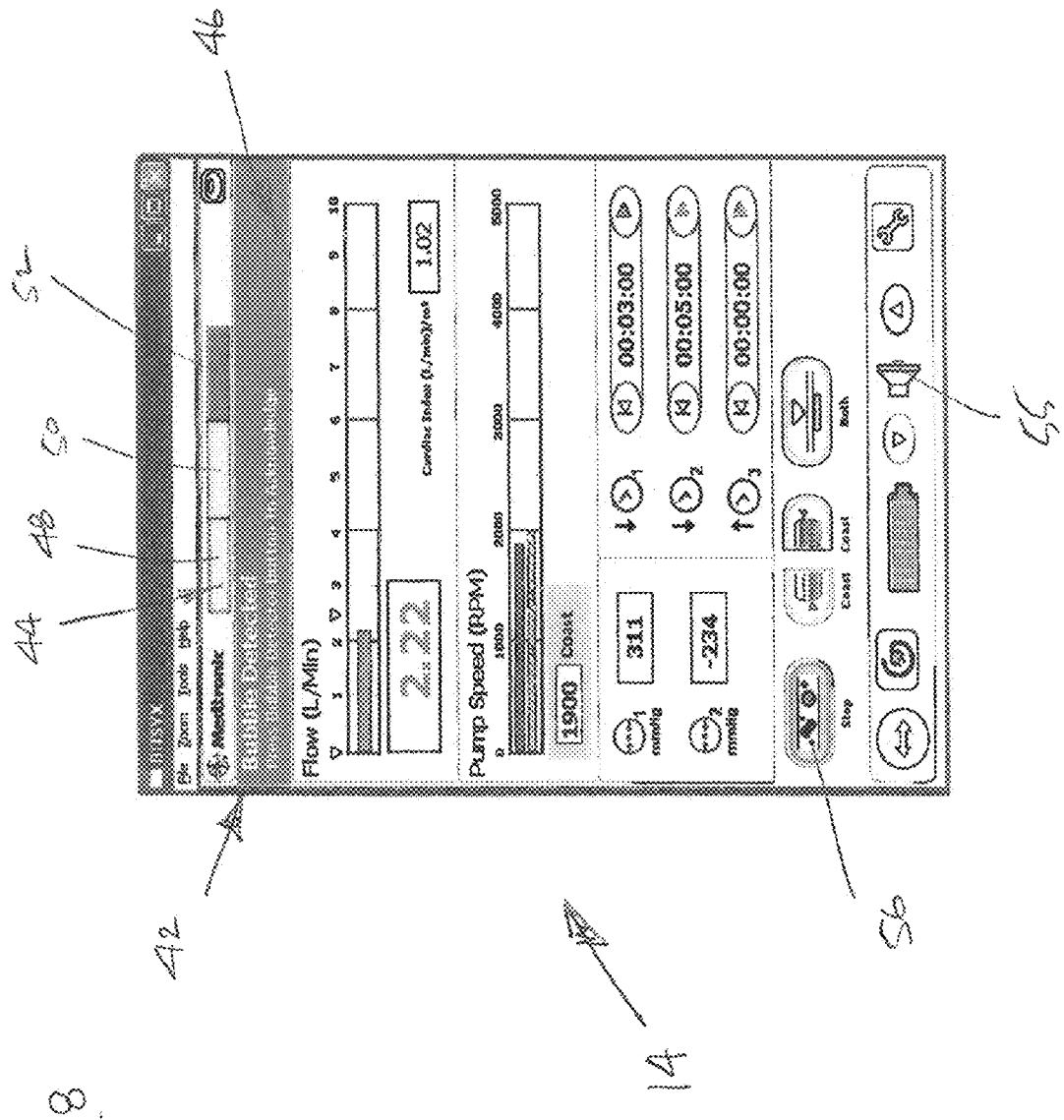
FIG. 8 illustrates a user interface in accordance with the present invention showing an alarm condition identified by a color-coded status bar and a color coded message box and showing color coded information for managing the alarm condition.

In FIG. 8, user interface 14 is illustrated in a state of alarm and with an indication of such alarm. An alarm condition is more serious than an alert condition and requires an immediate corrective action by the user. Exemplary alarm conditions relate to communications errors, bubbles in the flow circuit, and motor or pump failure. An alarm notification preferably includes a repeating sequence of long and short beeps and illumination of the red light bar 52 of the system status indicator 42, as illustrated. Light bars 48 and 50 are preferably unlit or colorless, as illustrated. Additionally, the system status message box 46 displays information about the alarm and is preferably displayed with a corresponding red color code. The illustrated alarm of FIG. 8 is related to detection of a bubble in the flow circuit, but any desired condition of the perfusion system can be characterized as an alarm condition. Accordingly the system status message box 46 identifies the condition and also provides information regarding how to manage the alarm with the words "Press Bubble Detector Button To Acknowledge." The alarm condition can be managed by pressing the service bubble detector button 56, which is also preferably color coded red with the alarm color. An alarm may display additional unique red icons to aid the user in identifying the source of the alarm condition. Accordingly, like the alert condition described above relative to FIG. 7, the user interface 14 provides an indication of the alarm with the red light bar 52 and red coded system status message box 46, indication of the particular condition and how to manage the condition in the system status message box 46, and an indication of where to manage the condition on the touch screen with the color coded icon. Any combination of colors, color intensity, sounds, and text can be used in accordance with the present invention to identify an alarm condition.

Figure 9:
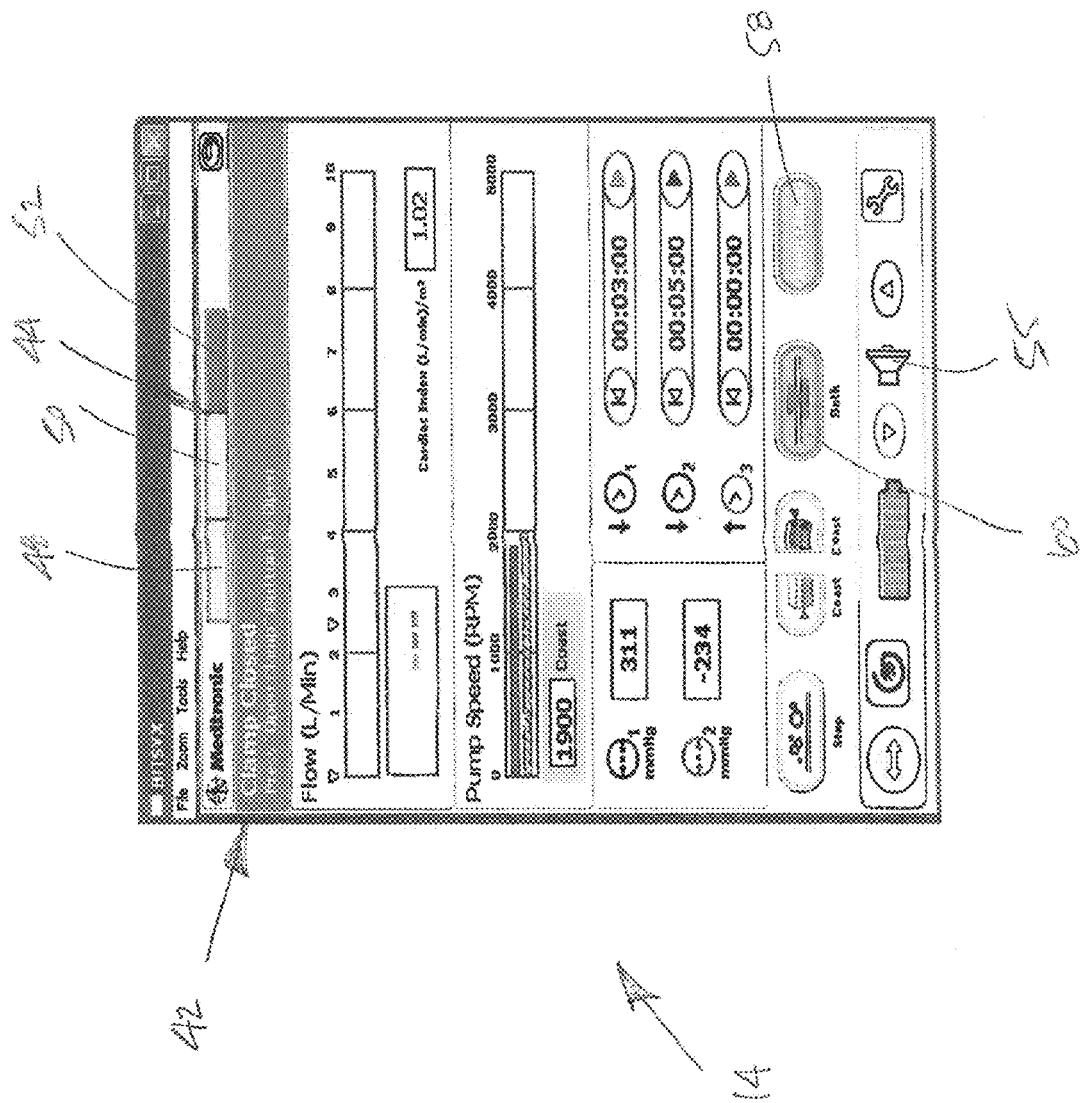
FIGS. 9 and 10 illustrate a user interface in accordance with the present invention showing another alarm condition identified by a color-coded status bar and a color coded message box and showing color coded information for managing the alarm condition.
Figure 10:
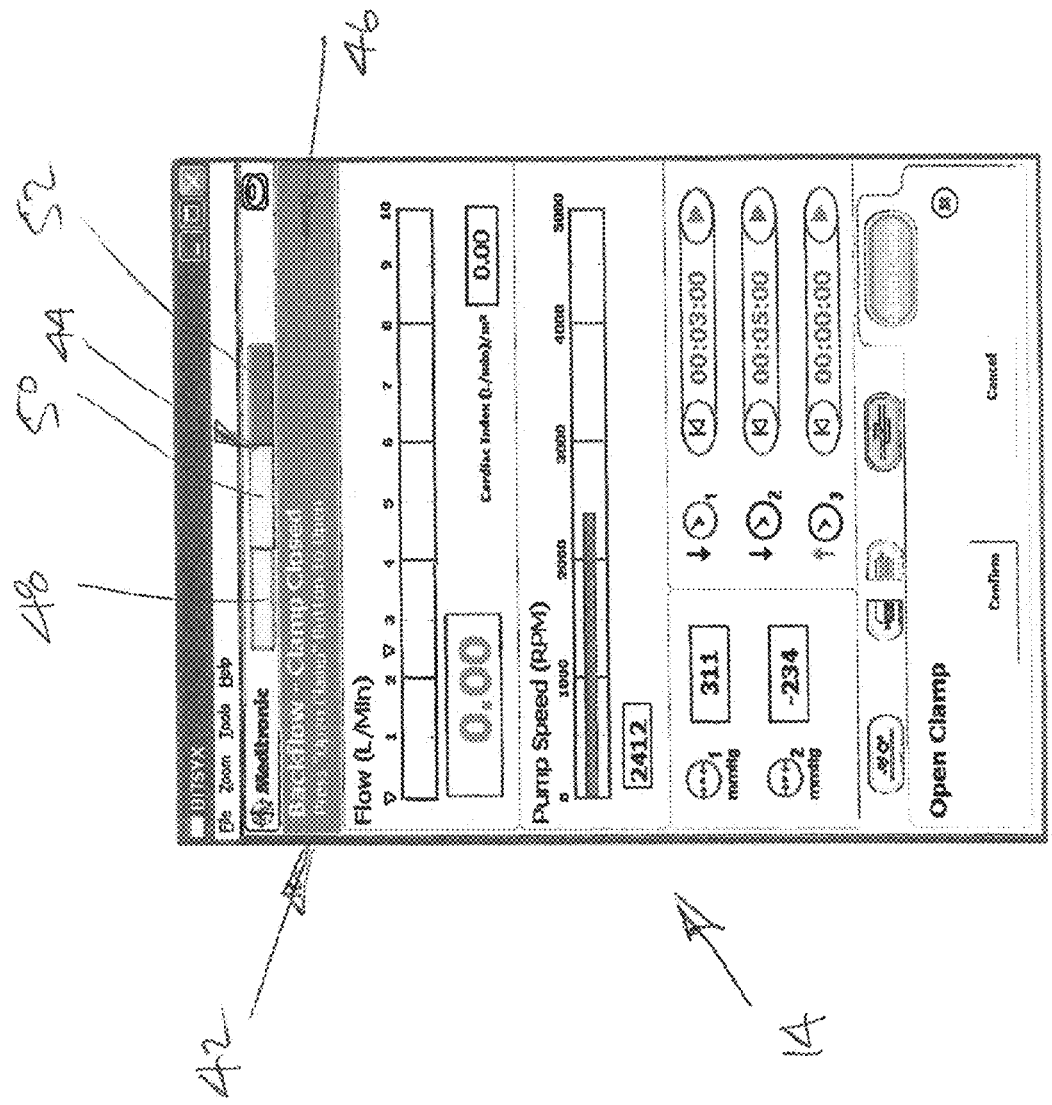

In FIGS. 9 and 10 another exemplary feature of the user interface 14 is illustrated. FIG. 9 shows user interface 14 in a state of alarm and with an indication of such alarm provided by illumination of the red light bar 52 of the system status indicator 42. In accordance with the present invention, the system status message box 46 displays information about the alarm and is preferably displayed with a corresponding red color code. In particular, the illustrated alarm of FIG. 26 is related to the state of a clamp system and indicates that the clamp is closed. Accordingly, the system status message box 46 identifies the condition and also provides information regarding how to manage the alarm by pressing the open clamp button 58 which is also preferably color coded red with the alarm color. Also illustrated is a clamp status button 60 color-coded red and which is used to configure the clamp system. In FIG. 10, a submenu 62 of the open clamp button 58 is shown which is activated and displayed when the open clamp button 58 is pushed and which can be used to provide verification of the action of opening the clamp by selecting a confirm button 64 or a cancel button 66.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of managing a condition change of a perfusion system during cardiopulmonary bypass surgery, the method comprising the steps of:

monitoring a perfusion control system during cardiopulmonary bypass surgery by way of a user interface of the perfusion control system comprising a display screen, the display screen showing a color coded system status bar that includes distinct bar portions, with one bar portion for displaying a first color, a second bar portion for displaying a second color, and a third bar portion for displaying a third color;

displaying the first color within the first portion of the color coded system status bar during normal operation of the perfusion system;

receiving information indicative an occurrence of a first system operational problem and a second system operational problem;

prioritizing the first and second system operational problems such that one of the first and second operational problems is designated as a highest priority system operational problem and the other of the first and second operational problems is designated as a next highest priority system operational problem;

displaying one of the second or third color within the respective second or third bar portion based upon the highest priority system operational problem, the color being displayed indicating any one out of a plurality of system conditions as have been prioritized according to a level of the system operation problem as such system operational problems have been programmed into the perfusion control system;

displaying a first message indicative of the highest priority system operational problem within a distinct system message box that is positioned separately from the status bar on the display screen, thereby indicating a specific system operation problem out of the plurality of system conditions that have been prioritized according to the level represented by the displayed color; and subsequently displaying a second message indicative of the next highest priority system operational problem within the distinct system message box upon correction of the highest priority system operational problem.

2. The method of claim 1, wherein the first, second, and third colors comprise green, yellow, and red, respectively.

3. The method of claim 2, wherein red indicates an alarm condition requiring immediate corrective action.

4. The method of claim 2, wherein yellow indicates an alert condition requiring non-immediate corrective action.

5. The method of claim 2, wherein green indicates absence of a requirement for corrective action.

6. The method of claim 1, further comprising a step of displaying a color coded system management icon on the display screen for managing the displayed system operational problem.

7. The method of claim 1, further comprising the step of displaying real time operating data indicators on the display screen.

8. A perfusion control system and a user interface for managing a condition change of a perfusion system during cardiopulmonary bypass surgery, the user interface comprising:

a display screen including a color coded system status bar that includes distinct bar portions, with one bar portion for displaying a first color, a second bar portion for displaying a second color, and a third bar portion for displaying a third color;

the display screen further including a coded textual message portion that is positioned separately from the status bar on the display screen for providing information related to a system operational problem, wherein each of the first, second, and third colors of the status bar indicate a distinct system condition; and the perfusion control system being programmed with system operational problems according to plural levels of severity with plural system operational problems prioritized as of an alert level and associated with the second color of the second bar portion and with plural operation problems prioritized as of an alarm level and associated with the third color of the third bar portion, the perfusion control system operatively connected with the display screen of the user interface so that under normal operation conditions the first color is displayed in the first bar portion, under the alert level of system operational problems the second color is displayed in the second bar portion and the coded textual message portion includes information of a specific operational problem of the alert level, and under the alarm level of system operational problems the third color is displayed in the third bar portion and the coded textual message portion includes information of a specific operational problem of the alarm level, wherein the perfusion control system is further programmed such that upon occurrence of a plurality of system operational problems, the display screen is prompted message in the coded textual message portion relating to a highest priority operational problem, followed by the display screen being prompted to display a second message in the coded textual message portion relating to a next highest priority operational problem upon correction of the highest priority operational problem.

9. The user interface of claim 8, wherein the display further comprises one or more color coded system management icons that are displayed positioned separately from the status bar and separately from the coded textual message portion on the display screen for managing a specific operational problem based on the color coded system status bar under an alert or alarm condition.

10. The user interface of claim 8, further comprising real time operating data indicators displayed on the display screen.

11. A pump console for use during cardiopulmonary bypass surgery, the pump console comprising a base unit and the perfusion control system with the user interface of claim 8, the base unit comprising one or more interfaces for controlling pump speed, monitoring flow, and communicating with the user interface.

12. The pump console of claim 11, further comprising one or more of an automated arterial line occlusion system, level detectors operatively connected to a blood reservoir, and a bubble detector system.

13. A method of managing a condition change of a perfusion system during cardiopulmonary bypass surgery, the method comprising the steps of:
monitoring a perfusion control system during cardiopulmonary bypass surgery by way of a user interface of the perfusion control system comprising a display screen, the display screen showing a color coded system status bar that includes distinct bar portions, with one bar portion for displaying a first color, a second bar portion for displaying a second color, and a third bar portion for displaying a third color;
displaying the first color within the first portion of the color coded system status bar during normal operation of the perfusion system, and subsequently displaying one of the second or third color within the respective second or third bar portion upon an occurrence of a system operational problem, the color being displayed indicating any one out of a plurality of system conditions as have been prioritized according to a level of the system operation problem as such system operational problems have been programmed into the perfusion control system;
displaying a message within a distinct system message box that is positioned separately from the status bar on the display screen and thereby indicating a specific system operation problem out of the plurality of system conditions that have been prioritized according to the level represented by the displayed color; and
displaying a color coded system management icon that is positioned separately from the status bar and separately from the system message box on the display screen for managing the displayed system operational problem based on the color coded system status bar under an alert or alarm condition.

14. The method of claim 13, wherein the first, second, and third colors comprise green, yellow, and red, respectively.

15. The method of claim 14, wherein red indicates an alarm condition requiring immediate corrective action.

16. The method of claim 14, wherein yellow indicates an alarm condition requiring non-immediate corrective action.

17. The method of claim 14, wherein green indicates absence of a requirement for corrective action.

18. The method of claim 13, wherein the step of displaying a color coded alarm condition on the display screen comprises displaying textual information to identify the alarm condition.

19. The method of claim 13, further comprising the step of displaying real time operating data indicators on the display screen.

* * * * *

UNITED STATES PATENT AND TRADEMARK OFFICE
CERTIFICATE OF CORRECTION

| | | |
|---|---|---|
| PATENT NO. | : 8,409,124 B2 | Page 1 of 1 |
| APPLICATION NO. | : 11/977916 | |
| DATED | : April 2, 2013 | |
| INVENTOR(S) | : Steffens et al. | |

It is certified that error appears in the above-identified patent and that said Letters Patent is hereby corrected as shown below:

In the Claims:

Column 7, line 23

"...is prompted message..."

should be changed to

--is prompted to display a first message--

Signed and Sealed this
Sixteenth Day of July, 2013

Teresa Stanek Rea
*Acting Director of the United States Patent and Trademark Office*